US006348044B1

United States Patent
Coletti et al.

(10) Patent No.: US 6,348,044 B1
(45) Date of Patent: Feb. 19, 2002

(54) METHOD AND APPARATUS FOR RECAPPING SINGLE-USE HYPODERMIC NEEDLES

(76) Inventors: George D. N. Coletti, 5417 E. Mountain St., Stone Mountain, GA (US) 30083; Walter W. Bond, 3366 Station Ct., Lawrenceville, GA (US) 30044

( * ) Notice: Subject to any disclaimer, the term of this patent is extended or adjusted under 35 U.S.C. 154(b) by 0 days.

(21) Appl. No.: 09/416,666

(22) Filed: Oct. 12, 1999

(51) Int. Cl.[7] ............................ A61M 5/32; B65D 83/10
(52) U.S. Cl. ..................... 604/192; 604/263; 206/365
(58) Field of Search ........................ 604/162, 164.08, 604/192, 263; 206/364–366, 370

(56) References Cited

U.S. PATENT DOCUMENTS

| | | |
|---|---|---|
| 4,717,386 A | 1/1988 | Simmons |
| 4,737,149 A | 4/1988 | Gillilan |
| 4,859,515 A * | 8/1989 | Pothetes ............ 428/40 |
| 4,979,945 A | 12/1990 | Wade et al. |
| 4,986,817 A | 1/1991 | Code |
| 5,078,695 A | 1/1992 | Farrar, Jr. et al. |
| 5,078,696 A | 1/1992 | Nedbaluk |
| 5,279,577 A | 1/1994 | Collett |
| 5,334,151 A | 8/1994 | Santilli |
| 5,358,111 A * | 10/1994 | Greenberg ............ 206/366 |
| 5,399,169 A | 3/1995 | Stein |
| 5,469,964 A | 11/1995 | Bailey |
| 5,607,403 A * | 3/1997 | Kretzschmar et al. ....... 604/263 |
| 5,769,223 A | 6/1998 | Marsh |
| 6,257,408 B1 * | 7/2001 | Odierno ............ 206/366 |

* cited by examiner

Primary Examiner—Sharon Kennedy
(74) Attorney, Agent, or Firm—Alston & Bird LLP

(57) ABSTRACT

An adhesive "block" device is provided which can be used to grip to removable caps of single-use, disposable, hypodermic needles. Adhesive is provided on four sides of the block allowing for the block to be attached at one side to a tray or other supporting surface, with at least one of the surfaces configured to easily deform, retain said deformation, and adhesively grip and immobilize the caps to allow for safe, "one-hand" removal and subsequent replacement of the needle in the cap.

12 Claims, 3 Drawing Sheets

METHOD AND APPARATUS FOR RECAPPING SINGLE-USE HYPODERMIC NEEDLES

TECHNICAL FIELD

The present invention generally relates to the medical industry, and particularly relates to a method and apparatus for safe, one-handed recapping (re-sheathing) and/or subsequent un-capping (un-sheathing) of single-use hypodermic needles.

BACKGROUND OF THE INVENTION

The prior art is replete with devices and methods for providing storage or other protection for a cap of a needle. The prior art likewise includes methods and apparatuses for providing "single-hand" attachment and detachment of caps from their respective needles. In particular, the prior art discloses the use of a clay-like or other "sticky" materials to insert grip the caps of needles, such as shown in Stein (U.S. Pat. No. 5,399,169) and Marsh (U.S. Pat. No. 5,769,223).

Particular attention is directed towards the Stein and the Marsh references. As may be seen, each of these references disclose the use of a deformable support material contained by a receptacle. In each of the patents the receptacle can be adhesively attached to a supporting surface by use of an adhesive (as an example see 36 in the Marsh patent).

Although the prior art includes advantages, needs still exist in the art.

SUMMARY OF THE INVENTION

The present invention overcomes deficiencies in the prior art by providing a disposable device which can be temporarily placed on a supporting surface to allow for one-handed uncapping and recapping of single use, disposable hypodermic needles.

Therefore it is an object of the present invention to provide an improved method and apparatus for safely handling single use, disposable hypodermic needles.

Therefore it is an object of the present invention to provide an improved method and apparatus for uncapping said hypodermic needles.

Therefore it is an object of the present invention to provide an improved method and apparatus for recapping said hypodermic needles.

Therefore it is an object of the present invention to provide an improved method and apparatus for handling said hypodermic needles which provides improved safety features.

Therefore it is an object of the present invention to provide an improved method and apparatus for handling said hypodermic needles which provides improved ergonomic features.

Therefore it is an object of the present invention to provide an improved method and apparatus for handling said hypodermic needles which provides improved cost and convenience features.

Other objects, features, and advantages of the present invention will become apparent upon reading the following detailed description of the preferred embodiment of the invention when taken in conjunction with the drawings and the appended claims.

DETAILED DESCRIPTION OF THE PREFERRED EMBODIMENT

Reference is now made to the drawings, in which like numerals indicate like elements throughout the several views.

General Construction and Operation

The invention generally relates to the use of an adhesive "block" device 10 which can be used to grip to removable caps of single use, disposable, hypodermic needles. Adhesive is provided on at least portions of, in one embodiment, four sides of the block 10 (see 11, 12, 13, and 14 of FIG. 5) allowing for the block to be attached at one side to a medical or dental instrument tray or other supporting surface, with these surfaces being configured to deform and adhesively grip the caps to allow for "one-hand" detachment and reattachment thereof.

Details on the Block

Figure 1:
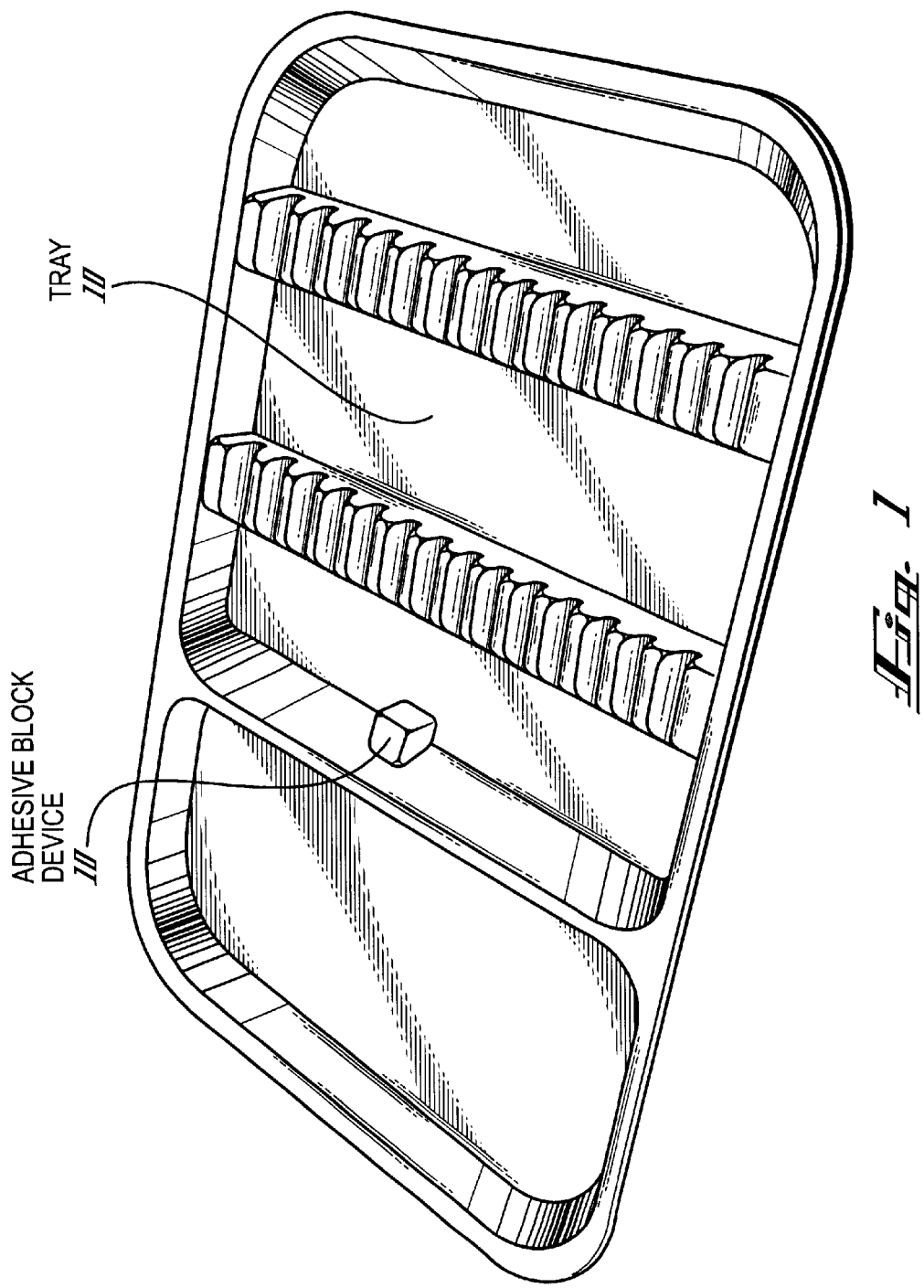
FIG. 1 is a pictorial view of an adhesive block device 10 according to the present invention attached within a medical-dental instrument tray 20. No needles or caps are shown in place in this drawing.
Figure 2:
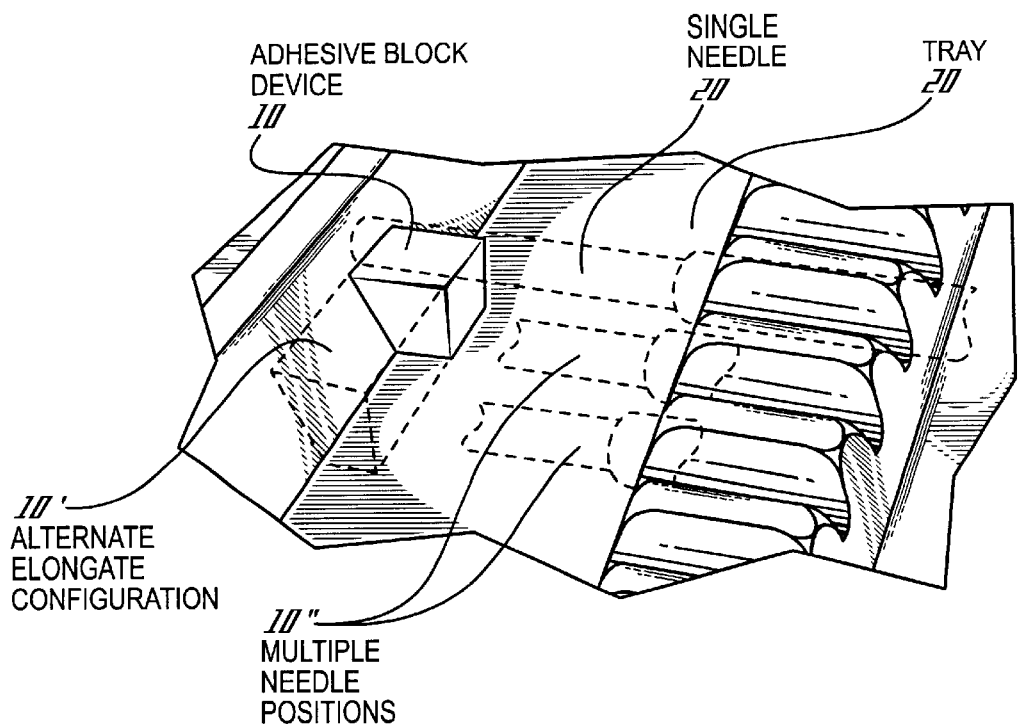
FIG. 2 is a more detailed view of a portion of that shown in FIG. 1, with an alternate block configuration shown in phantom as 10'. A single capped needle 20 which would be used with the device 10 is shown in phantom as 20, and additional multiple capped needles which would be used with the alternate elongate configuration are shown as 10".

Reference is first made to FIGS. 1 and 2. FIG. 1 is a pictorial view of an adhesive block device 10 according to the present invention attached within a medical or dental instrument tray 20. No capped needles are shown in place in this drawing. FIG. 2 is a more detailed view of a portion of that shown in FIG. 1.

As may be seen, an "adhesive block" 10 is provided, which provides a block which can be used to grip the caps of said hypodermic needles. In one embodiment, four sides of the block include surface adhesive, allowing for the block to be attached to said tray or other flat supporting surface, and to attach itself to the caps. The cap-contacting surface is not only sticky, but is also deformable and has some memory while allowing the deformation to be retained upon light to moderate downward pressure.

In one embodiment, one "inclined" side can be at an angle to allow for use within a tray having an angled side wall. It is highly preferable that the dimensions are selected such that the block protrudes slightly above the tray lip to accommodate such deformation during needle cap placement in proximity of the tray wall.

Figure 5:
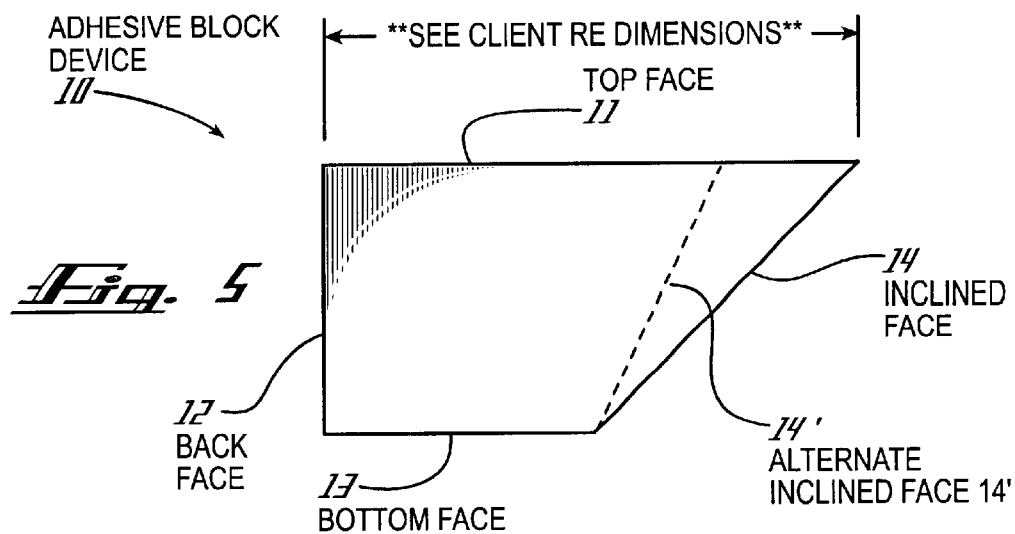
FIG. 5 is a isolated view of the adhesive block according to the present invention. Height and angle may be modified for production to conform to a particular tray.

The device 10 is intended to be utilized on either flat surfaces or on tray walls with an angulation of approximately 45 degrees. The top of the adhesive block will give a flat surface for the needle cap to rest upon horizontally. The 45 degree angle is intended to stick to the side of medical/dental instrument trays which have a 45 degree angle. However, as shown in FIG. 5, other configurations are contemplated without departing from the spirit and scope of the present invention.

Figure 6:
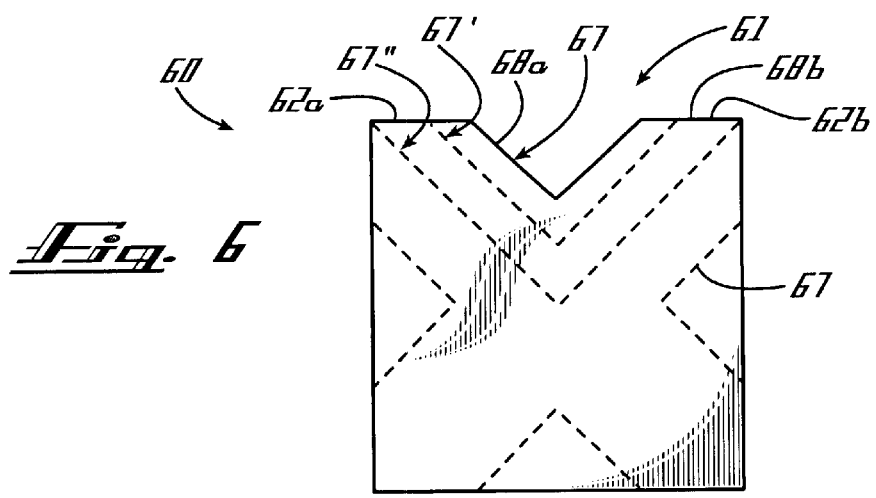
FIG. 6 is an illustrative view of an alternate notched block configuration 60 in which one or more of the four sides having adhesive thereon include notches or grooves such as 67, 67', or 67" on any or all of the adhesive-provided sides. One side 61 includes surface portions or faces 62a, 62b, 68a, and 68b. Faces 68a and 68b are formed by notch 67.
Figure 4:
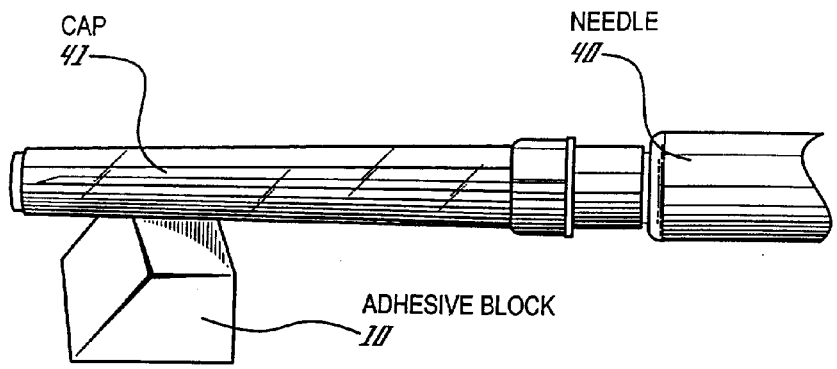
Figure 5:
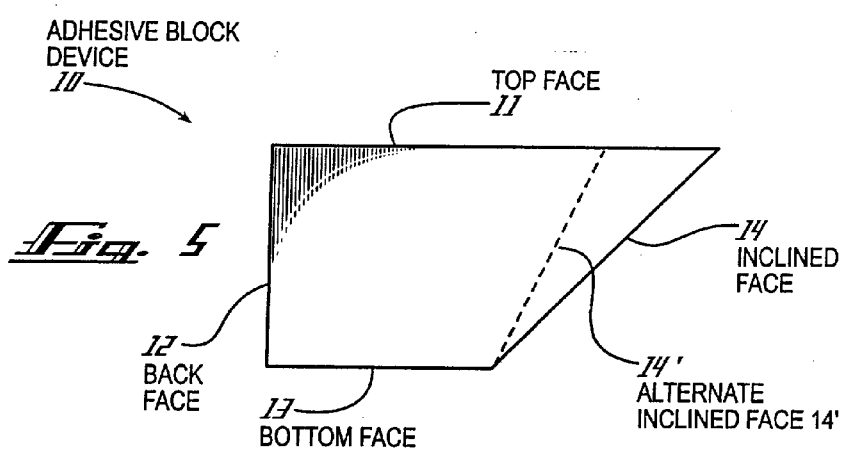
Figure 6:
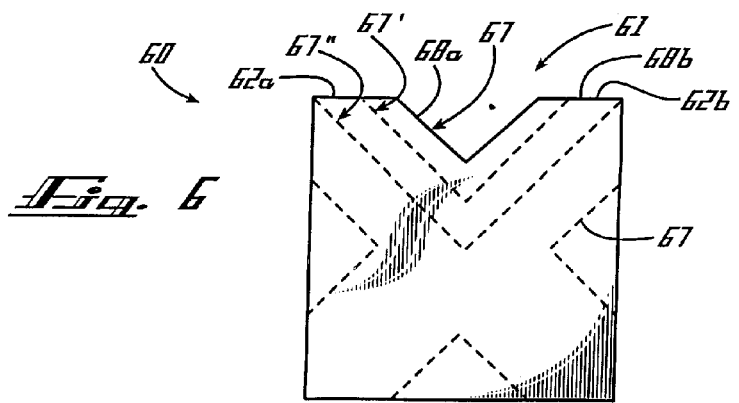
Figure 1:
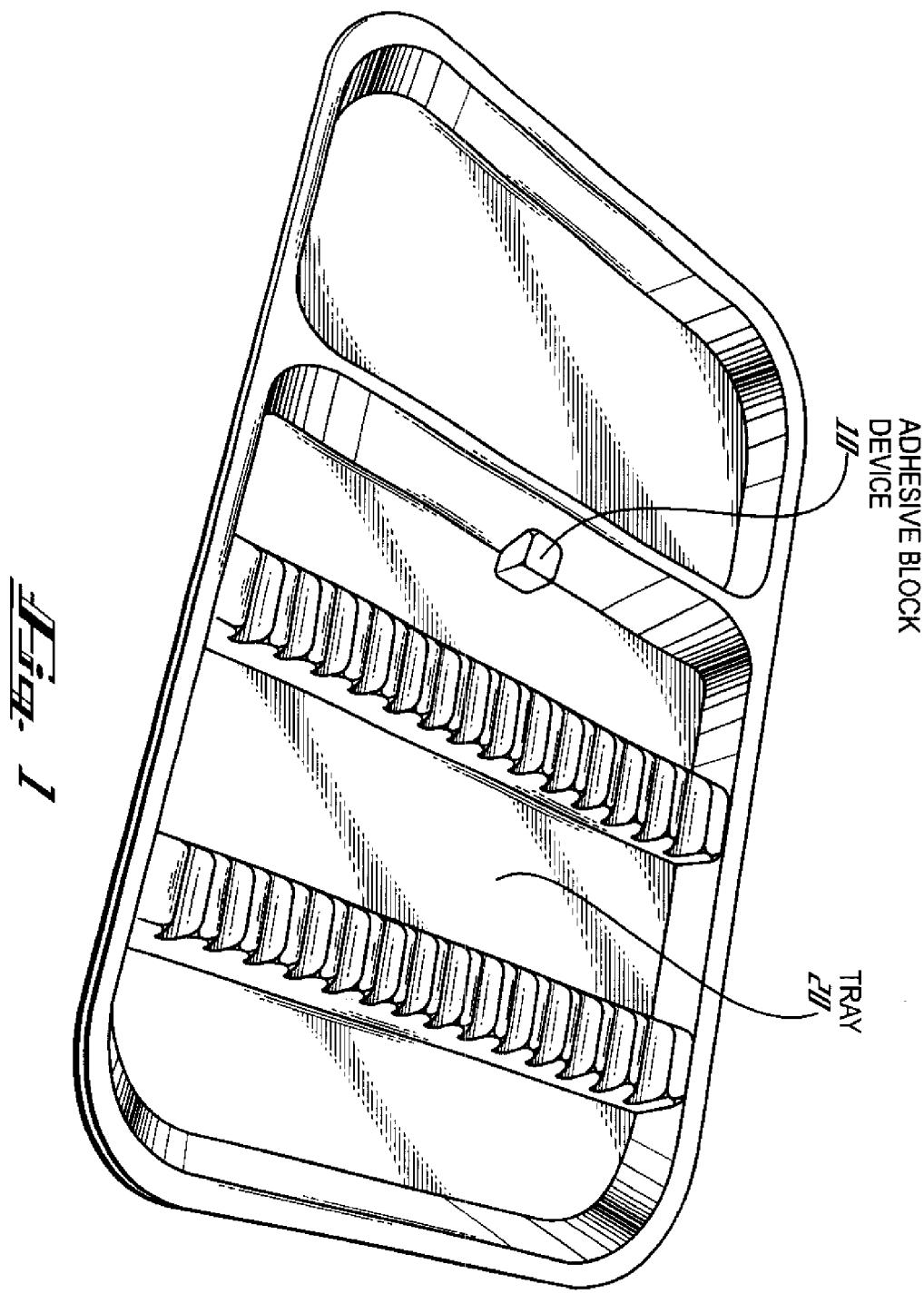

It should be understood that the present invention discusses the provision of various "sides" to the adhesive block 10. The term side is intended to mean a surface or collection of surfaces which are all generally oriented in the same direction. In FIG. 2, the block has six sides, which are all planar. All of these sides consist of one common planar "face". However, in FIG. 6, some of the sides include multiple surface portions or "faces", which combine to comprise each side. In FIG. 6, the side 61 includes surface portions or faces 62a, 62b, 68a, and 68b.

Figure 3:
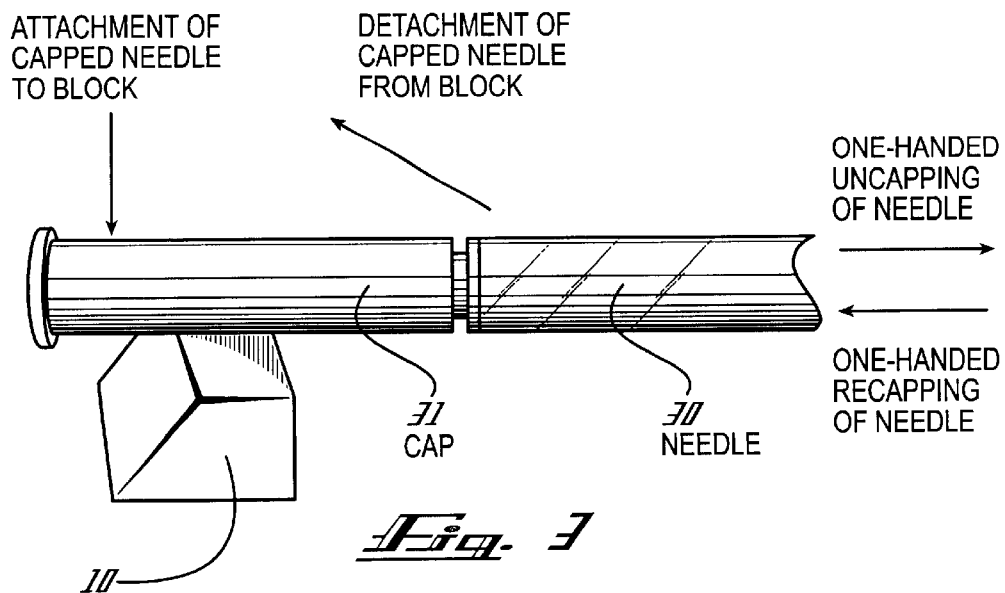
FIG. 3 is a pictorial view of a first embodiment needle 30 having a cap 31, used in conjunction with a block 10 according to the present invention. Any of the four adhesive surfaces of the block can be used to attach the block to a flat surface. Various relative movements between the adhesive block and the needle are also shown.
Figure 4:
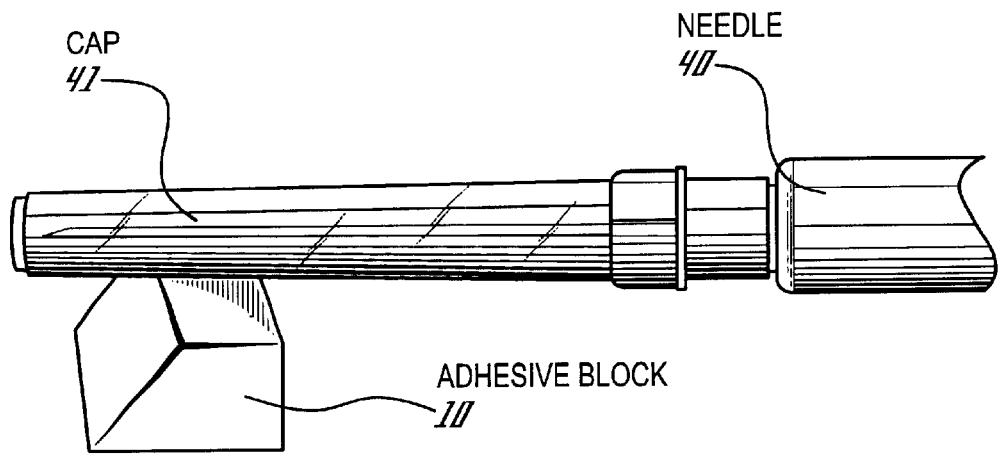
FIG. 4 is a pictorial view of a second embodiment needle 40 having a cap 41, used in conjunction with a block 10 according to the present invention. The dimensions are variable according to the size of the needle cap and number of caps requiring immobilization, and the surface to which the demobilization device is attached.

Reference is now made to FIGS. 3 and 4. FIG. 3 is a pictorial view of a first embodiment needle 30 having a cap 31, used in conjunction with a block 10 according to the present invention. FIG. 4 is a pictorial view of a first embodiment needle 40 having a cap 41, used in conjunction with a block 10 according to the present invention. Various relative movements between the adhesive block and the needle are also shown. As may be seen by these two figures, the block according to the present invention is configured to attach to a variety of needle or needle cap designs.

Details on Operation

FIG. 3 shows the various movements which may be used to allow for attachment, detachment, decapping of needles and recapping of needles.

Movement in the "A" direction, assisted with moderate direct finger pressure causes attachment of the capped needle to the block accompanied by deformation of the block material to conform to the outside dimensions of the needle cap surface. Movement in the "B" direction causes detachment of the capped needle from the block.

Movement in the "C" direction, accompanied with continued moderate finger pressure allows for initial one-handed uncapping of the needle. This allows for one-handed un-capping of the needle after the initial "seal" is broken manually. Movement in the "D" direction allows for one-handed recapping of the needle.

It should be understood that the device 10 should have sufficient adhesive ability to resist between two and one half and three pounds of pressure before the needle cap is terminally released from the adhesive block prior to disposal.

Composition

The material to which the adhesive is attached should allow approximately three to five millimeters (3–5 mm) of sponginess and displaying minimum elastic memory when placing the needle cap on the device.

The type of material used for this could be Styrofoam or a dense sponge, or any other suitable material known in the art.

Alternate Embodiments

An alternate embodiment includes the concept of having the adhesive manufactured directly onto the needle cap and when the needle cap placed on a surface for in use one-handed decapping and recapping (after initial decapping).

Another alternate configuration is contemplated under which a plurality of capped needles may be placed on one more elongate block. Referencing FIG. 2, phantom lines show the alternate configuration, in which a more elongate block is configured to attach to and support a plurality of capped needles arranged side-by-side in the tray.

FIG. 6 is an illustrative view of an alternate block configuration in which the four sides having adhesive thereon include notches or "V"-grooves such as 67, 67', or 67" on any or all of the adhesive-provided sides. Such grooves can be configured to accept the round outline of the needle caps.

It should be understood that although the above invention has been described in conjunction with single-use, disposable items, it could be used more than once to the extent allowed by proper medical standards.

Conclusion

While this invention has been described in specific detail with reference to the disclosed embodiments, it will be understood that many variations and modifications may be effected within the spirit and scope of the invention as described in the appended claims.

We claim:

1. A method for attaching a hypodermic needle to a supporting surface, said needle having an elongate cap having opposing ends and at least one side extending along its length, said method comprising the steps of:
   A) providing a deformable block having multiple sides, at least a portion of each of two of said sides including adhesive thereon;
   B) attaching said deformable block to said supporting surface;
   C) attaching said cap and said needle as a unit to said block such that said side of said cap is attached to said deformable block; and
   D) detaching said cap from said needle with said cap remaining attached to said block.

2. The method as claimed in claim 1, wherein during step "A", said deformable block is further provided to include a third side including a corresponding third side portion being substantially flat and including adhesive thereon, such that said elongate cap of said hypodermic needle may be detachably fixed to one of said first, second, or third side portions of said block, and one of the remaining two side portions of said block may be detachably fixed to said supporting surface and supported thereby.

3. The method as claimed in claim 2, wherein during step "A", said deformable block is further provided such that two of its said flat side surface portions are adjacent and at right angles to each other.

4. The method as claimed in claim 2, wherein during step "A", said deformable block is further provided such that two of said flat side surface portions are oppositely facing and the third is an intermediate perpendicular, inclined, flat side surface portion.

5. The method as claimed in claim 1, wherein during step "A", said deformable block is further provided such that said deformable block further includes third and fourth sides including corresponding third and fourth side portions each being substantially flat and including adhesive thereon, such that said elongate cap of said hypodermic needle may be detachably fixed to one of said first, second, third, or fourth side portions of said block, and one of the remaining three side portions of said block may be detachably fixed attached to said supporting surface and supported thereby.

6. The method as claimed in claim 5, wherein during step "A", said deformable block is further provided wherein said four side portions are in pairs in parallel planes.

7. The method as claimed in claim 5, wherein during step "A", said deformable block is further provided such that each of said four side portions comprise the entirety of each of said four side portions.

8. The method as claimed in claim 1, wherein during step "A", said deformable block is further provided such that said first side portion is provided in part by a V-shaped groove in said first side, and wherein during step "C" said side is at least partially within said groove.

9. The method as claimed in claim 1, wherein during step "C", said deformable block is deformed as said cap and said needle are attached as a unit to said block.

10. A method for attaching a hypodermic needle to a supporting surface of a needle tray, said needle having an elongate cap having opposing ends and at least one side extending along its length, said method comprising the steps of:

A) providing a deformable block having multiple sides, at least a portion of each of two of said sides including adhesive thereon;

B) attaching said deformable block to said supporting surface of said needle tray;

C) attaching said cap and said needle as a unit to said block such that said side of said cap is attached to said deformable block; and D) detaching said cap from said needle with said cap remaining attached to said block.

11. A method for attaching a hypodermic needle to a supporting surface of a needle tray, said needle having an elongate cap having opposing ends and at least one side extending along its length, said method comprising the steps of:

A) providing a deformable block having multiple sides, at least a portion of each of two of said sides including adhesive thereon;

B) attaching said deformable block to a supporting surface of said needle tray;

C) attaching said cap and said needle as a unit to said block such that said die of said cap is attached to said deformable block; and D) detaching said cap from said needle with said cap remaining attached to said block; and E) reattaching said cap to said needle with said cap remaining attached to said block.

12. A method for attaching a hypodermic needle to a supporting surface of a needle tray including a supporting floor surface and also including a plurality of adjacent needle body cradling portions, said needle having a body and also having an elongate separable cap having opposing ends and at least one side extending along its length, said method comprising the steps of:

A) providing a deformable block having multiple sides, at least a portion of each of two of said sides including adhesive thereon;

B) attaching said deformable block to said supporting surface of said needle tray;

C) attaching said cap and said needle as a unit to said block such that said side of said cap is attached at to said deformable block and said needle body is cradled by one of said needle body cradling portion; and D) detaching said cap from said needle with said cap remaining attached to said block.

* * * * *

UNITED STATES PATENT AND TRADEMARK OFFICE
CERTIFICATE OF CORRECTION

PATENT NO. : 6,348,044 B1
DATED : February 19, 2002
INVENTOR(S) : Coletti et al.

It is certified that error appears in the above-identified patent and that said Letters Patent is hereby corrected as shown below:

Title page,
Item [57], ABSTRACT,
Line 2, "to", second occurrence, should read -- the --.

Drawings,
Sheet 3 should be deleted to be substituted with the attached sheet 3, as shown on the attached page.

Column 4,
Line 62, cancel "attached".

Column 6,
Line 5, cancel "and";
Line 23, cancel "at".

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.   : 6,348,044 B1
DATED        : February 19, 2002
INVENTOR(S)  : Coletti et al.

It is certified that error appears in the above-identified patent and that said Letters Patent is hereby corrected as shown below:

Drawings,
Figure 1, "Tray 10" should read -- "Tray 20" --.
Replace Figure 1 with attached Figure 1.

Column 3,
Line 25, "first" should read -- second --.

Signed and Sealed this

Second Day of November, 2004

JON W. DUDAS
*Director of the United States Patent and Trademark Office*